United States Patent
Yung et al.

(10) Patent No.: US 10,654,789 B2
(45) Date of Patent: May 19, 2020

(54) CATALYST AND METHOD FOR BIODIESEL PRODUCTION FROM UNREFINED LOW-GRADE OIL AND CRUDE AQUEOUS ALCOHOLS

(71) Applicant: The Hong Kong Polytechnic University Shenzhen Research Institute, Shenzhen (CN)

(72) Inventors: Ka-fu Yung, Shenzhen (CN); Wing-tak Wong, Shenzhen (CN); Tsz-lung Kwong, Shenzhen (CN); Pak-chung Lau, Shenzhen (CN)

(73) Assignee: THE HONG KONG POLYTECHNIC UNIVERSITY SHENZHEN RESEARCH INSTITUTE, Shenzhen (CN)

( * ) Notice: Subject to any disclaimer, the term of this patent is extended or adjusted under 35 U.S.C. 154(b) by 0 days.

(21) Appl. No.: 15/920,811

(22) Filed: Mar. 14, 2018

(65) Prior Publication Data

US 2018/0265446 A1     Sep. 20, 2018

Related U.S. Application Data

(60) Provisional application No. 62/471,192, filed on Mar. 14, 2017.

(51) Int. Cl.
    *C07C 67/03*      (2006.01)
    *C07C 67/02*      (2006.01)
    (Continued)

(52) U.S. Cl.
    CPC ............ *C07C 67/03* (2013.01); *B01J 31/223* (2013.01); *B01J 31/2208* (2013.01);
    (Continued)

(58) Field of Classification Search
CPC ......... C07C 67/02; C07C 67/03; C07C 67/08; C11C 3/04; B01J 2231/49; B01J 2531/49; B01J 2531/842; B01J 2531/845
See application file for complete search history.

(56) References Cited

U.S. PATENT DOCUMENTS

| | | | |
|---|---|---|---|
| 4,943,316 A * | 7/1990 | Taylor | C07C 29/70 204/157.43 |
| 7,420,073 B2 * | 9/2008 | Hillion | C07C 67/03 554/167 |

(Continued)

OTHER PUBLICATIONS

Bartunek, V., et al., CoO and Co3O4 nanoparticles with a turnable particle size, 2014, Ceramics International, vol. 40, pp. 12591-12595 (Year: 2014).*

(Continued)

*Primary Examiner* — Yate' K Cutliff
(74) *Attorney, Agent, or Firm* — Leydig, Voit & Mayer, Ltd.

(57) ABSTRACT

A catalyst for catalyzing transesterification of esters or esterification of fatty acids, the catalyst is selected from the group consisting of manganese (II) glycerolate, cobalt (II) glycerolate, iron (II) glycerolate, and any combination thereof. A method for transesterification reaction, includes: a) providing a catalyst, wherein the catalyst is selected from the group consisting of manganese (II) glycerolate, cobalt (II) glycerolate, iron (II) glycerolate, and any combination thereof; b) adding the catalyst, one or more alcohols, and a composition comprising one or more esters to a reactor to form a reaction mixture; and c) stirring while heating the reaction mixture for reaction to form transesterification products.

20 Claims, 3 Drawing Sheets

(51) Int. Cl.
*C07C 67/08* (2006.01)
*B01J 31/22* (2006.01)
*C11C 3/04* (2006.01)
*C11C 3/00* (2006.01)
*B01J 37/34* (2006.01)
*B01J 31/02* (2006.01)

(52) U.S. Cl.
CPC .............. *B01J 37/346* (2013.01); *C07C 67/02* (2013.01); *C07C 67/08* (2013.01); *C11C 3/003* (2013.01); *C11C 3/04* (2013.01); *B01J 31/0212* (2013.01); *B01J 2231/49* (2013.01); *B01J 2531/72* (2013.01); *B01J 2531/842* (2013.01); *B01J 2531/845* (2013.01); *Y02E 50/13* (2013.01)

(56) References Cited

U.S. PATENT DOCUMENTS

| 7,563,915 B2* | 7/2009 | Matson | C11C 3/003 |
| | | | 44/388 |
| 8,124,801 B2* | 2/2012 | Srinivas | B01J 23/28 |
| | | | 554/169 |
| 2009/0134369 A1* | 5/2009 | Dutta | B01J 19/02 |
| | | | 252/601 |

OTHER PUBLICATIONS

Jankovsky, O., et al., Synthesis of MnO, Mn2O3 and Mn3O4 nanocrystal clusters by thermal decomositon of manganese glycerolate, 2015, Ceramics International, vol. 41, pp. 595-601 (Year: 2015).*
John Wiley & Sons, Kirk-Othnner, Encyclopedia of Chemical Technology, Fourth Edition, vol. 10, 1993, abstract 3 pages (Year: 1993).*
Radoslovich, E.W., et al., Crystalline cobalt, zinc, manganese and iron alkoxides, 1970, Australian Journal of Chemistry, vol. 23, No. 10, pp. 1963-1971 (Year: 1970).*
Reinoso, D.M., et al., Zinc glycerolate as a novel heterogeneous catalyst for the synthesis of fatty acid methyl esters, 2013, Applied Catalysis B: Environmental, vol. 144, pp. 308-316 (Year: 2013).*
Rodrique, L., et al., High temperature syntehsis of iron glycerolate through ferrous and ferric oxalate, 1978, Powder Technology, 19(1), pp. 93-101 (Year: 1978).*
Salimon J. et al., Physicochemical Properties of Malaysian Jatropha curcas Seed Oil, 2008, Sains Malaysiana 37(4), pp. 379-382 (Year: 2008).*
Slade, P.G., et al., Crystal and molecular structure of Cobalt (II) Monoglycerolate, 1971, Acta Crystallographica, Section B: Structural Crystallography and Crystal Chemistry, 27(Pt. 12), pp. 2432-2436 (Year: 1971).*

* cited by examiner

US 10,654,789 B2

CATALYST AND METHOD FOR BIODIESEL PRODUCTION FROM UNREFINED LOW-GRADE OIL AND CRUDE AQUEOUS ALCOHOLS

CROSS-REFERENCE TO RELATED APPLICATIONS

This application claims priority to pending U.S. Provisional Application No. 62/471,192 filed on Mar. 14, 2017, the content of which is incorporated by reference herein in its entirety.

TECHNICAL FIELD

The present application relates to biodiesel production, and more particularly to a catalyst and a method for biodiesel production from unrefined low-grade oil and crude aqueous alcohols, and a method for catalyst preparation.

BACKGROUND

Biodiesel is a non-toxic, carbon neutral renewable fuel which is generally produced by transesterification of oil feedstock with short chain alcohols and exhibits similar physical and chemical properties to conventional diesel fuel. Biodiesel may curtail the harmful emissions such as NOx, SOx, CO, $CO_2$, unburnt hydrocarbon, and particulates.

The conventional production of biodiesel through transesterification involves the breaking down of a triglyceride molecule with alcohols to yield biodiesel and glycerol in the presence of catalyst. Conventional production of biodiesel often involves a homogeneous strong acid (e.g. HCl or $H_2SO_4$) or strong base (e.g. KOH or NaOH).

The production cost for the transesterification of refined plant oil is 1.5 times higher than that of conventional diesel fuel. It is advantageous that the development of biodiesel production from waste oil or low grade feedstock through transesterification directly would reduce the production cost. The waste oil and low grade feedstock often contain a high degree of free fatty acids ("FFAs") and water content which hinder the transesterification process. The high water content in low grade feedstock may result in hydrolysis of triglyceride to produce FFAs while the FFAs would subsequently react with the base catalyst to yield soaps that complicate the separation of glycerol from the catalytic system and thus, it suppresses the transesterification reaction.

To overcome this issue, a two-step process is used to produce biodiesel from low grade feedstock or waste oil. The first step of the two-step process involves the pretreatment step of FFAs removal by an acidic catalyst (e.g. HCl or $H_2SO_4$) followed by a second step of an alkaline (e.g. KOH or NaOH) catalyzed transesterification. These homogeneous strong acids and bases are highly corrosive and require a large amount of fresh water for biodiesel purification and generate an enormous amount of waste water and thus, the production cost is increased. Although this two-step operation may utilize the low grade feedstock and waste oil, the process requires multiple washing steps and leads to loss of catalyst.

SUMMARY

In view of the above-described problems, among others, one of the objectives of the present application is to provide a catalyst and a method for biodiesel production from unrefined low-grade oil and crude aqueous alcohols through one-step simultaneous esterification and transesterification, and a method for preparing the catalyst.

To achieve the above objective, in accordance with one embodiment of the present application, there is provided a catalyst for catalyzing transesterification of esters or esterification of fatty acids, and the catalyst is selected from the group consisting of manganese (II) glycerolate ("MnGly"), cobalt (II) glycerolate ("CoGly"), iron (II) glycerolate ("FeGly"), and any combination thereof.

In accordance with another embodiment of the present application, there is provided a method for preparing a catalyst, and the method comprises:

a) dissolving one or more metal acetate precursors into glycerol to yield a reaction mixture, wherein each of the one or more metal acetate precursors comprises cations being selected from manganese (II), cobalt (II), iron (II);

b) placing the reaction mixture in a pressurized microwave synthesis system for reaction; and c) centrifuging a resulting precipitate, washing a centrifuged product with ethanol, and drying a resulting product to yield the catalyst, whereupon the catalyst is the one from the group consisting of manganese (II) glycerolate, cobalt (II) glycerolate, iron (II) glycerolate, and any combination thereof.

In accordance with still another embodiment of the present application, there is provided a method for transesterification reaction, and the method comprises:

a) providing a catalyst, wherein the catalyst is selected from the group consisting of MnGly, CoGly, FeGly, and any combination thereof;

b) adding the catalyst, one or more alcohols, and a composition comprising one or more esters to a reactor to form a reaction mixture; and c) stirring while heating the reaction mixture for reaction to form transesterification products.

The heterogeneous catalyst system of the present application involves a one-step process of simultaneous esterification and transesterification and has high tolerance to water and free fatty acids, thus being beneficial to increase the flexibility for various low grade feedstocks selected in biodiesel production which reduces production costs.

BRIEF DESCRIPTION OF THE DRAWINGS

Exemplary embodiments of the invention are described herein below with reference to the accompanying drawings.

DETAILED DESCRIPTION OF THE ENABLING EMBODIMENTS

Figure 1:
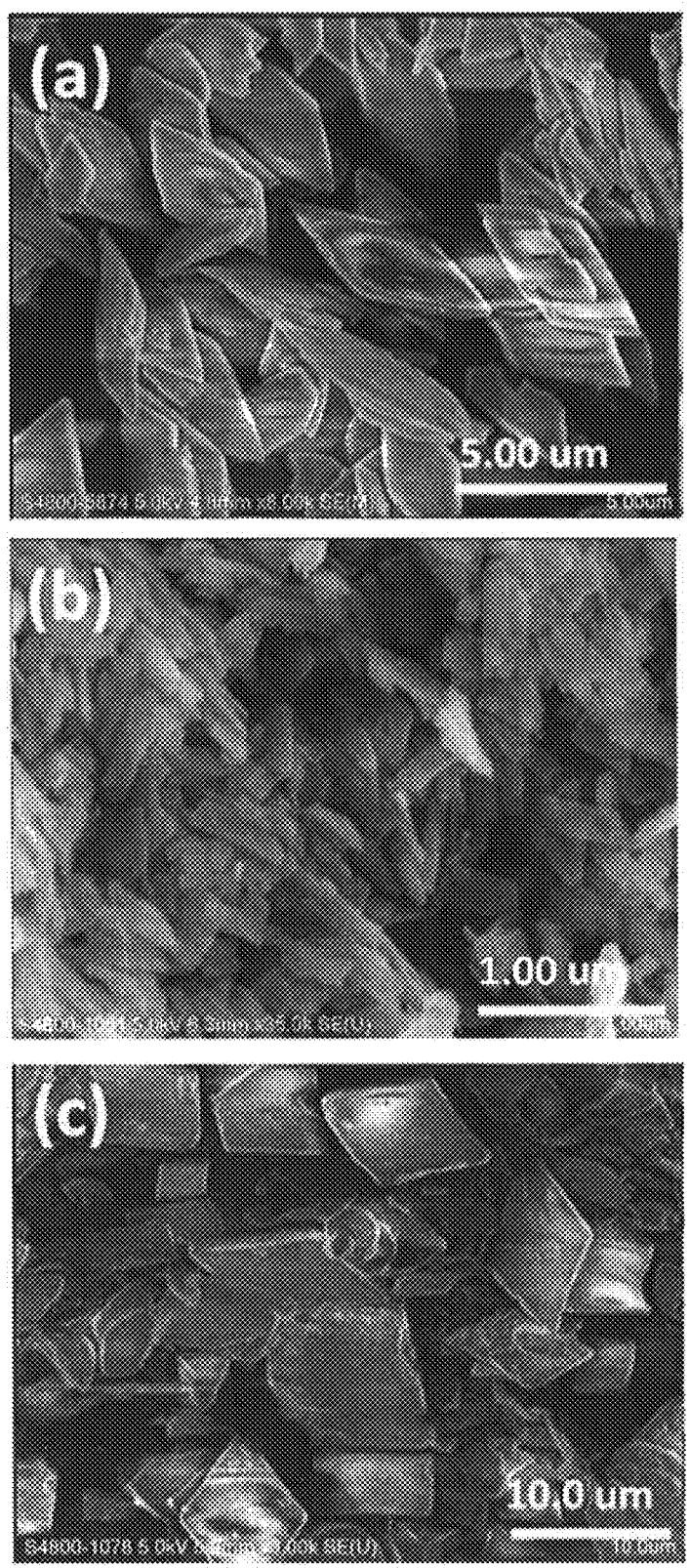
FIG. 1 shows electron scanning electron microscope ("SEM") micrographs. Specifically, part (a) of FIG. 1 is a SEM micrograph of (a) MnGly in accordance with one embodiment of the present application; part (b) of FIG. 1 is a SEM micrograph of (a) FeGly in accordance with one embodiment of the present application; and part (c) of FIG. 1 is a SEM micrograph of (a) CoGly in accordance with one embodiment of the present application.

For further illustrating the invention, experiments detailing a catalyst and a method for biodiesel production from unrefined low-grade oil and crude aqueous alcohols, and a method for catalyst preparation are described below. It should be noted that the following examples are intended to describe and not to limit the invention.

In accordance with one embodiment, the present application provides a catalyst for catalyzing transesterification of esters or esterification of fatty acids, and the catalyst is selected from the group consisting of manganese (II) glycerolate (MnGly), cobalt (II) glycerolate (CoGly), iron (II) glycerolate (FeGly), and any combination thereof.

In one embodiment, the catalyst is in a solid form with a dimension of between 0.05 μm and 50 μm.

In accordance with another embodiment, the present application provides a method for preparing a catalyst, and the method comprises:
a) dissolving one or more metal acetate precursors into glycerol to yield a reaction mixture, wherein each of the one or more metal acetate precursors comprises cations being selected from manganese (II), cobalt (II), iron (II);
b) placing the reaction mixture in a pressurized microwave synthesis system for reaction; and
c) centrifuging a resulting precipitate, washing a centrifuged product with ethanol, and drying a resulting product to yield the catalyst, whereupon the catalyst is selected from the group consisting of manganese (II) glycerolate, cobalt (II) glycerolate, iron (II) glycerolate, and any combination thereof.

In one embodiment, a molar number of glycerol is at least 20 times of a molar number of the one or more metal acetate precursors. In another embodiment, the molar number of glycerol is at least 35 times of the molar number of the one or more metal acetate precursors.

In one embodiment, a reaction temperature of step b) is at least about 80° C. In a preferred embodiment, the reaction temperature of step b) is between about 100° C. and about 200° C.

In one embodiment, a reaction time of step b) is at least about 15 min. In a preferred embodiment, the reaction time of step b) is between about 1 and about 8 hrs.

In one embodiment, a reaction pressure is between about 1 and about 30 psi. In a preferred embodiment, the reaction pressure is between 5 and 30 psi.

In one embodiment, a microwave power is at least 100 Watts. In a preferred embodiment, the reaction pressure is between 100 and 300 Watts.

In accordance with still another embodiment, the present application provides a method for transesterification reaction, and the method comprises:
a) providing a catalyst, wherein the catalyst is selected from the group consisting of MnGly, CoGly, FeGly, and any combination thereof;
b) adding the catalyst, one or more alcohols, and a composition comprising one or more esters to a reactor to form a reaction mixture; and
c) stirring while heating the reaction mixture for reaction to form transesterification products.

In one embodiment, the one or more alcohols is selected from the group consisting of methanol, ethanol, propanol, butanol, pentanol, hexanol, heptanol, octanol, and any isomers thereof.

In one embodiment, the one or more esters may be triglycerides, wherein fatty acid portions of the triglycerides may be selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-y-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid, and octatriacontanoic acid.

In one embodiment, the one or more esters may be a biodiesel feedstock. In one embodiment, the one or more ester may comprise plant-based oil, gutter oil, and grease trap waste. The plant-based oil may comprise *Jatropha* oil, *Camelina* oil, canola oil, soy bean oil, corn oil, and/or palm oil. As used herein "gutter oil" refers to cooking oil which has been recycled from waste oil collected from sources such as restaurant fryers, sewer drains, grease traps, and slaughterhouse waste. As used herein, "grease trap waste" refers to grease from a plumbing device designed to catch grease and solids before they enter a wastewater disposal system.

In one embodiment, the composition comprising one or more esters may further comprise one or more free fatty acids selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-y-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid, and octatriacontanoic acid for enhancing a reaction rate and conversion of the one or more esters.

In one embodiment, the reaction mixture is heated to a temperature of between about 100° C. and about 300° C. for reaction. In one embodiment, the reaction mixture is heated to a temperature of least about 120° C. In one embodiment, the reaction mixture is heated to a temperature of least about 130° C. In one embodiment, the reaction mixture is heated to a temperature of least about 140° C. In one embodiment, the reaction mixture is heated to a temperature of least about 150° C.

In one embodiment, the number of moles of the one or more alcohols is at least 6 times of the number of moles of the composition comprising one or more esters.

In one embodiment, an addition of the catalyst is between about 2 and about 10 wt. %, based on a weight of the composition comprising one or more esters.

In one embodiment, the one or more free fatty acids account for between about 0.1 and about 100 wt. % of the composition comprising one or more esters. In a preferred embodiment, the one or more free fatty acids account for at least about 3 wt. % of the composition comprising one or more esters.

In one embodiment, the water content in each of the one or more alcohols is between 0 and about 80 wt. %, based on the weight of each of the one or more alcohols. In one embodiment, a water content in each of the one or more alcohols is between about 1 and about 80 wt. %, based on the weight of each of the one or more alcohols.

Example 1 Preparation of Catalysts

A series of metal glycerolate catalysts, manganese (II) glycerolate (MnGly), cobalt (II) glycerolate (CoGly), and iron (II) glycerolate (FeGly), were synthesized by dissolving $(CH_3COO)_2Mn \cdot 4H_2O$ (0.5 g, 2.04 mmol), $(CH_3COO)_2Co \cdot 4H_2O$ (0.5 g, 2.01 mmol), and $(CH_3COO)_2Fe$ (0.5 g, 2.88 mmol) into glycerol (12.5 mL) respectively. The reaction mixture was placed into the pressurized microwave synthesis system (DISCOVER™ SP, CEM Corporation) at 200° C. for 2 hrs in which the microwave system was operated at 250 W at a fixed power mode. The resulting precipitate was centrifuged, washed with ethanol three times and finally dried at 80° C. The metal glycerolate catalysts were obtained in solid forms.

Example 2 Characterization of Catalysts

The above series of metal glycerolate catalysts (MnGly, CoGly, and FeGly) isolated in the solid forms were respectively analyzed by Powder X-ray diffraction (XRD) patterns, Hitachi S-4800 field electron scanning electron microscope (SEM), Fourier transform infrared (FTIR) spectrum, and Hammett indicator analysis.

1) Results of Electron Scanning Electron Microscope (SEM)

The size and morphology of the metal glycerolates were analyzed by electron scanning electron microscope (SEM) operating at 5 kV. As shown in FIG. 1, MnGly (part (a) of FIG. 1), CoGly (part (c) of FIG. 1) are found to adopt layered platelet structures while FeGly (part (b) of FIG. 1) adopts a rod-shaped structure. Among all metal glycerolates prepared, MnGly shows the most regular structure which exhibits a regular parallelogram-shaped thin plate morphology with an average dimension of 3.16±0.31 μm×2.38±0.25 μm, and CoGly and FeGly are relatively less regular in shape with uneven sizes. The average dimensions of the three metal glycerolates are shown in Table 1.

TABLE 1

Average dimensions of metal glycerolates

| Catalysts | Average Dimension |
| --- | --- |
| MnGly | 3.16 μm × 2.38 μm |
| CoGly | 6.98 μm × 5.26 μm |
| FeGly | 0.55 μm × 0.15 μm |

2) Results of Powder X-Ray Diffraction (XRD) Patterns

Figure 2:
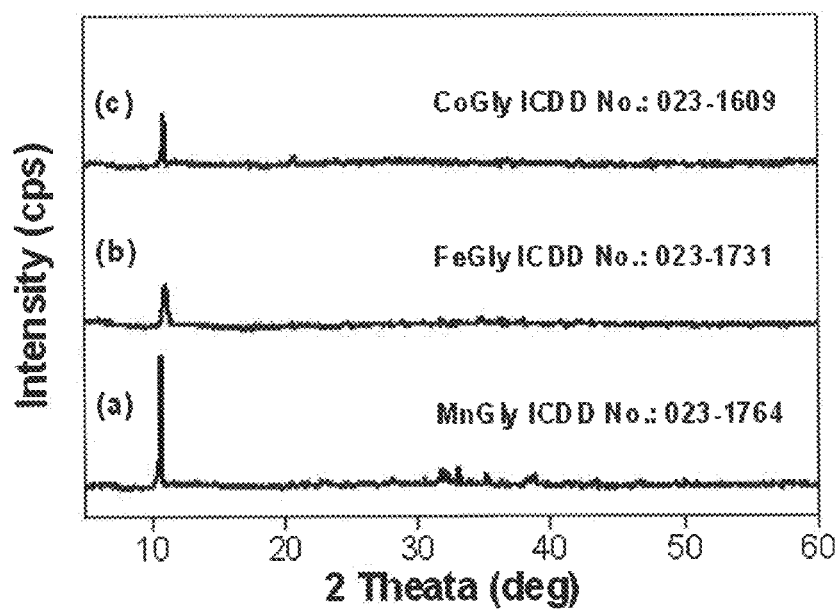
FIG. 2 shows powder X-ray diffraction ("XRD") spectra. Specifically, part (a) of FIG. 2 is a XRD spectra of (a) MnGly in accordance with one embodiment of the present application; part (b) of FIG. 2 is a XRD spectra of (a) FeGly in accordance with one embodiment of the present application; and part (c) of FIG. 2 is a XRD spectra of (a) CoGly in accordance with one embodiment of the present application.

As shown in FIG. 2, the characteristic diffraction peaks of the as-synthesized MnGly (part (a) of FIG. 2), FeGly (part (b) of FIG. 2), and CoGly (part (c) of FIG. 2) are matched with standard diffraction patterns according to the ICDD card No. 023-1764, 023-1731, 023-1609 respectively. The crystallinity of FeGly and CoGly are relatively lower than that of MnGly as observed from the smaller peak heights in the diffraction patterns of FeGly and CoGly.

3) Results of Fourier Transform Infrared (FTIR) Spectrum

Figure 3:
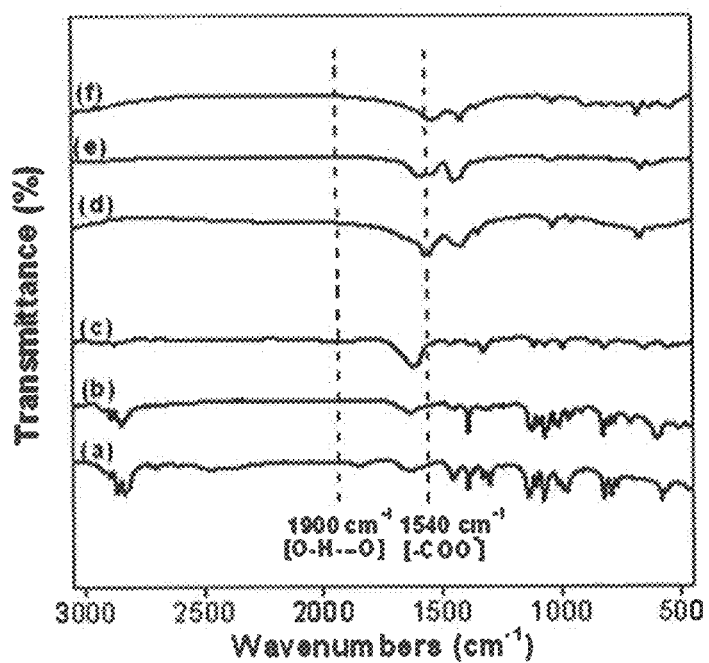
FIG. 3 shows fourier transform infrared ("FTIR") spectra in accordance with one embodiment of the present application. Specifically, part (a) of FIG. 3 is a FTIR spectra of MnGly in accordance with one embodiment of the present invention; part (b) of FIG. 3 is a FTIR spectra of FeGly in accordance with one embodiment of the present invention; part (c) of FIG. 3 is a FTIR spectra of CoGly in accordance with one embodiment of the present invention; part (d) of FIG. 3 is a FTIR spectra of $(CH_3COO)_2Mn$ in accordance with one embodiment of the present invention; part (e) of FIG. 3 is a FTIR spectra of $(CH_3COO)_2Fe$ in accordance with one embodiment of the present invention; and part (f) of FIG. 3 is a FTIR spectra of $(CH_3COO)_2Co$ in accordance with one embodiment of the present invention.

FIG. 3 shows the FTIR spectra of all the metal glycerolates and their respective metal acetate precursors. The appearance of weak signal at around 1900 $cm^{-1}$ is ascribed to the stretching vibrations of C—O bond where the oxygen atom is involved in the O—H—O hydrogen bonding which is missing from the spectra of their respective metal acetates. On the other hand, the absence of signal at 1540 $cm^{-1}$ due to anti-symmetric stretching of C—O bond on the carboxylate (—$COO^-$) group further confirms the complete transformation of metal acetate precursors into metal glycerolates.

4) Results of Hammett Indicator Analysis

Based on the result of Hammett indicator analysis as shown in Table 2, the surface basic strength of MnGly and CoGly were found to be in the range of $6.8 < H_{13} < 7.2$ which demonstrate amphoteric property on the surface of the three metal glycerolates. FeGly gave a lower surface basic strength in the range of $4.8 < H_{13} < 6.8$ which is slightly acidic in nature.

TABLE 2

Hammett indicator analysis of metal glycerolates

| Metal glycerolate | Surface basic strength |
| --- | --- |
| MnGly | $6.8 < H\_ < 7.2$ |
| FeGly | $4.8 < H\_ < 6.8$ |
| CoGly | $6.8 < H\_ < 7.2$ |

Example 3 Catalytic Activities of Metal Glycerolate Catalysts Towards Biodiesel Production from Crude *Jatropha* Oil Catalytic activities of different metal glycerolate catalysts (MnGly, CoGly, and FeGly) towards one-step simultaneous esterification and transesterification reaction of crude *Jatropha* oil with methanol were analyzed as follows:

Different catalysts (MnGly, CoGly, and FeGly) were respectively added to a stirred batch reactor containing crude *Jatropha* oil and pure methanol to yield a reaction mixture, in which, a molar ratio of the *Jatropha* oil to the methanol was 1:20, a catalyst loading was 6 wt. %, based on a weight of the *Jatropha* oil. The reaction was heated with a constant stirring at 750 rpm at a reaction temperature of 140° C. for 8 hrs. Thereafter, the synthesized biodiesel layer was separated from the catalyst by centrifugation.

The feedstock conversions were analyzed by $^1$H nuclear magnetic resonance (NMR) spectroscopy on Bruker 400 MHz spectrometer using CDCl$_3$ as solvent. The feedstock conversions were calculated based on the integrated ratio of the signal of —OCH$_2$ on fatty acid ethyl ester ("FAEE") over that of the α-CH$_2$ on triglyceride and FAEE as follows:

$$\text{Conversion} = \frac{I_{-OCH2}}{I_{\alpha-CH2}} \times 100$$

The feedstock conversions are listed in Table 3. As shown in Table 3, in the one-step biodiesel production from *Jatropha* oil and methanol, MnGly exhibited the highest catalytic activity with 99.7% feedstock conversion in 8 hrs, and CoGly and FeGly showed feedstock conversions of 51.7% and 8.4% respectively.

TABLE 3

Catalytic activities of metal glycerolates towards one-step biodiesel production from crude *Jatropha* oil

| Catalyst | Conversion | |
|---|---|---|
| | Methanol[a] | Ethanol[b] |
| MnGly | 99.7 | 95.8 |
| CoGly | 51.7 | 50.5 |
| FeGly | 8.4 | 12.0 |

NOTE:
[a]Reaction condition: feedstock-to-alcohol molar ratio (1:20), catalyst loading (6 wt. %), reaction temperature (140° C.) and reaction time (8 hrs).
[b]Reaction condition: feedstock-to-alcohol molar ratio (1:20), catalyst loading (6 wt. %), reaction temperature (150° C.) and reaction time (4 hrs).

The catalytic activities of different metal glycerolate catalysts (MnGly, CoGly, and FeGly) towards one-step simultaneous esterification and transesterification reaction of crude *Jatropha* oil with ethanol were analyzed. Specifically, different catalysts (MnGly, CoGly, and FeGly) were respectively added to a stirred batch reactor containing crude *Jatropha* oil and pure ethanol to yield a reaction mixture, in which, a molar ratio of the feedstock-to-ethanol was 1:20, a catalyst loading was 6 wt. %, based on the weight of the crude *Jatropha* oil. The reaction was heated with the constant stirring at 750 rpm at the reaction temperature of 150° C. for 4 hrs. Thereafter, the synthesized biodiesel layer was separated from the catalyst by centrifugation. The feedstock conversion results are listed in Table 3. As shown in Table 3, in the one-step biodiesel production from *Jatropha* oil and ethanol, MnGly exhibited the highest catalytic activity with 95.8% feedstock conversion in 4 hrs, and CoGly and FeGly showed feedstock conversions of 50.5% and 12.0% respectively.

The relatively lower catalytic performance of CoGly and FeGly could be ascribed to the low crystallinity as shown from the XRD analysis. Moreover, it is reported that amphoteric catalyst is desirable for one-step esterification and transesterification reaction due to the presence of both Lewis acid and base catalytic sites. Therefore, the catalytic activities of amphoteric MnGly and CoGly were better than that of acidic FeGly which requires harsher reaction conditions.

On the other hand, the coordination geometry of metal glycerolates is proposed to be one of the factors affecting their catalytic activities towards FAEE production. The coordination geometry of different metal complexes varies with the type of ligands bonded and the coordination preference of metal center. Since Mn$^{2+}$ adopts high spin d$^5$ electronic configuration, there is only a small change in its crystal field stabilization energies between the tetrahedral and octahedral geometries. As a result, MnGly is believed to show no coordination preference for tetrahedral or octahedral geometries, implying that MnGly exhibits flexible coordination geometry to form stable transition state involving the conversion of tetrahedral to octahedral to tetrahedral state during the catalytic cycle as proposed in the transesterification mechanism. However, as Fe$^{2+}$ and Co$^{2+}$ show d$^6$ and d$^7$ electronic configuration respectively that possess preferred geometry, there may be a mismatch in the transition state geometry formed. The coordination preference of metal center may cause a destabilization in the transient yield which impairs the overall catalytic activity. This may explain why MnGly demonstrated higher catalytic activities than FeGly and CoGly.

Example 4 Catalytic Activity of MnGly Towards Simulated Bioethanol of Different Water Content Since MnGly gave the best performance towards biodiesel production from crude *Jatropha* oil with ethanol or methanol among all metal glycerolates, MnGly was chosen for further investigation on its catalytic activity towards aqueous bioethanol.

The presence of water in crude bioethanol is usually regarded as a detrimental factor towards biodiesel production. The interaction between catalyst surface and water molecules is one of the major causes of inhibition of a heterogeneous catalyst as the water molecules adsorb on the catalyst surface. This eventually blocks access of reactants to the catalyst and reduces the rate of the reaction. Further, the presence of surface bounded water may induce the hydrolysis of triglycerides into fatty acids which is another critical factor limiting the yield of biodiesel. As a result, the dehydration and purification of bioethanol is a crucial process for biodiesel application which is an energy-intensive and complex process with high production cost.

Therefore, the water tolerance of MnGly catalyst towards biodiesel production from crude *Jatropha* oil and simulated bioethanol of different water content was examined. A series of 95 to 20 wt. % aqueous ethanol were generated by the addition of 5 to 80 wt. % water into absolute ethanol respectively to simulate the water content in bioethanol. Reaction operations were the same as that of the one-step simultaneous esterification and transesterification reaction of crude *Jatropha* oil with ethanol using MnGly as the catalyst in Example 3, the reaction temperature was 150° C., the feedstock-to-ethanol molar ratio was 1:20, and catalyst loading was 6 wt. %, based on the weight of the feedstock. In addition, the one-step production from refined canola oil with 7.5 wt. % oleic acid and simulated bioethanol of different water content using MnGly as the catalyst was also examined. The conversion results are listed in Table 4.

TABLE 4

Catalytic activity of MnGly towards biodiesel production from simulated bioethanol of different water content

| | Conversion$^a$ (%) | | | |
|---|---|---|---|---|
| | Crude Jatropha oil | | Refined canola oil with 7.5 wt. % oleic acid | |
| Ethanol (wt. %) | 5 hrs | 10 hrs | 5 hrs | 10 hrs |
| 100 | 99.1 | — | 99.9 | — |
| 95 | 93.8 | 99.8 | 94.4 | 99.9 |
| 90 | 86.9 | 99.6 | 87.7 | 99.5 |
| 85 | 82.3 | 99.3 | 82.1 | 99.5 |
| 80 | 80.4 | 99.6 | 79.1 | 99.3 |
| 75 | 76.4 | 98.8 | 76.6 | 99.6 |
| 70 | 72.5 | 99.0 | 73.6 | 99.5 |
| 60 | 68.9 | 98.3 | 70.1 | 98.5 |
| 50 | 65.2 | 98.2 | 68.3 | 98.0 |
| 40 | 62.0 | 92.5 | 62.6 | 91.1 |
| 30 | 57.3 | 86.5 | 60.0 | 87.0 |
| 20 | 50.6 | 71.7 | 52.6 | 71.8 |

NOTE:
$^a$Reaction conditions: reaction temperature (150° C.), feedstock-to-ethanol molar ratio (1:20) and catalyst loading (6 wt. %).

As shown in Table 4, for the biodiesel production from the Crude *Jatropha* oil, a decreasing trend in the feedstock conversion was observed from 93.8 to 50.6% when the water content in ethanol increased from 5 to 80 wt. % under the same reaction time of 5 hrs. The use of 95 wt. % ethanol was commonly reported to cause a drastic decline in biodiesel yield but its application to MnGly catalytic system has only led to a slight reduction in the conversion from 99.1% to 93.8% when compared to absolute ethanol. Based on the high catalytic activity of MnGly towards the FAEE synthesis using 95 wt. % ethanol as source, we extended this study to further investigate its reactivity for ethanol containing higher percentage of water in prolong time. Upon prolonging the reaction time to 10 hrs, the catalyst can withstand 50 wt. % water in ethanol with feedstock conversion over 98%. Even when the water content in ethanol was increased to 80 wt. %, the conversion can still achieve 71.7%. Although longer reaction time was required to obtain higher conversion, these findings support the fact that MnGly produces FAEE that fulfills the EN 14214 (standard published by the European Committee for Standardization that describes the requirements for methanol fatty acid methyl esters) standard yield requirement (at least 96.5% alkyl ester present in the biodiesel) even there is 50 wt. % of water present in the ethanol used.

In literature, so far there is no other heterogeneous metal oxide based catalyst reported can achieve such high water tolerance for FAEE synthesis. This could be attributed to the fact that the active sites of common base heterogeneous catalyst, such as alkaline earth metal oxides, can easily be poisoned by chemisorption of water and carbon dioxide, resulting in the inhibition of the catalysts. The exceptionally high water tolerance of MnGly towards biodiesel production could be attributed to the adsorption of oleic acid on the catalyst surface, enhancing the surface hydrophobicity. The hydrophobic catalyst surface would repel hydrophilic water molecules so as to protect the catalyst from water inhibition.

Example 5 Application of Different Crude Bioethanol Sources Towards Biodiesel Production Crude bioethanol generated from fermentation of carbohydrates usually achieves roughly 20 wt. % of aqueous ethanol solution. As MnGly catalytic system has confirmed to exhibit an excellent water tolerance up to 80 wt. % in ethanol, this catalytic system can be applied to some low-cost non-refined renewable bioethanol sources. In order to evaluate the utilization of crude bioethanol on MnGly catalytic system, an artificially made aqueous ethanol sample comprising of 80 wt. % water was applied to simulate the high water containing crude bioethanol with a feedstock conversion of 91.5% after 24 hrs. After that, two commercially available low grade bioethanol samples were studied under the same reaction conditions as described in Table 5. The use of singly distillated rice wine composed of 24.4 wt. % ethanol was found to have a remarkable conversion of 98.9% after 24 hrs while the application of crude glutinous rice wine of 14.1 wt. % ethanol containing 10 wt. % glucose showed a conversion of 88.5%.

TABLE 5

Comparison on application of different bioethanol sources towards MnGly and NaOH catalyzed biodiesel production.

| | Conversion$^a$ (%) | | | |
|---|---|---|---|---|
| | MnGly$^b$ | | NaOH$^c$ | |
| Ethanol source | 5 h | 24 h | 5 h | 24 h |
| Artificially made 20 wt. % ethanol | 50.5 | 91.5 | 7.5 | 33.0 |
| Rice wine (24.4 wt. % ethanol) | 57.2 | 98.9 | 7.6 | 38.4 |
| Glutinous rice wine (14.1 wt. % ethanol) | 24.4 | 88.5 | 5.8 | 30.6 |

NOTE:
$^a$Reaction conditions: reaction temperature (150° C.), feedstock-to-ethanol molar ratio (1:20) and oleic acid loading (3 wt. %).
$^b$MnGly loading (6 wt. %).
$^c$ NaOH loading (1 wt. %).

For comparison, 1 wt. % of NaOH was applied as homogeneous catalyst towards biodiesel production with the three bioethanol sources, a gradual decrease in feedstock conversions was observed as summarized in Table 5. Even the reaction time was prolonged to 24 hrs, NaOH failed to catalyze FAEE production from crude bioethanol with feedstock conversions less than 40%. The negative impact of water on NaOH catalyzed biodiesel production could be ascribed to the occurrence of saponification.

As a result, MnGly has proved to be a robust catalyst that overcomes the negative influence of water in crude bioethanol which can be applied directly towards biodiesel production.

Figure 4:
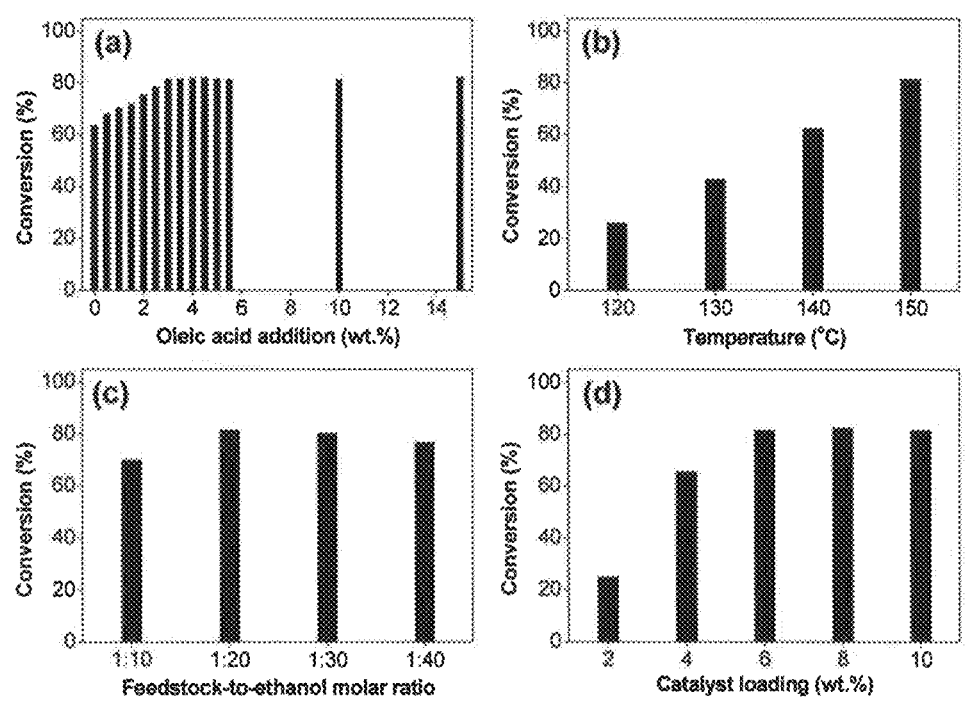
FIG. 4 shows the effects of reaction parameters on the catalytic activity of MnGly. Specifically, part (a) of FIG. 4 shows the effect of oleic acid content on MnGly catalyzed biodiesel production using 95 wt. % ethanol; part (b) of FIG. 4 shows the effect of reaction temperature; part (c) of FIG. 4 shows the effect of the feedstock-to-ethanol molar ratios; and part (d) of FIG. 4 shows the catalyst loading on MnGly catalyzed one-step simultaneous esterification and transesterification with 95 wt. % ethanol and 3 wt. % of oleic acid.

Example 6 Catalytic Activity of MnGly Towards Feedstock of Different Free Fatty Acid (FFA) Content Further analysis on the effect of FFA content in feedstock was done by the addition of different weight amount of oleic acid as model of FFA into refined food grade canola oil and the result is depicted in part (a) of FIG. 4. It is observed that the feedstock conversion increased steadily from 63.6% to 81.6% when the oleic acid content increased from 0 wt. % to 3 wt. %. No further increment was observed beyond 3 wt. % of oleic acid added. The initial enhancement of feedstock conversion confirmed the existence of one-step simultaneous esterification and transesterification reaction in the presence of FFA in feedstock. As the reaction begins, the FFA would adsorb on the catalyst surface and esterification of the FFA proceeds prior to transesterification of triglyceride. The high rate of esterification is attributed to the higher solubility of FFA in alcohol than that of triglyceride and the lower activation energy for esterification than transesterification. Upon exceeding the critical point (3 wt. %), the catalyst surface is saturated with FFA so that the addition of more FFA up to 15 wt. % does not cause any improvement in the overall conversion. Therefore, the application of any non-refined feedstock containing 3 wt. % FFA or above in this catalytic system could maximize the rate of biodiesel production.

In order to investigate the effect of FFA content in feedstock on the catalytic activity of MnGly towards simulated bioethanol on the water tolerance, an artificially generated feedstock composing of refined food grade canola oil and 7.5 wt. % oleic acid (50% higher FFA content than crude *Jatropha* oil) was applied to the catalytic system to see if it will enhance or retard the conversion in the presence of more water. It was found that similar feedstock conversions were attained from all entries as that from crude *Jatropha* oil within 3% derivations as demonstrated from Table 4. It seems that once the amount of FFA present is increased to 3 wt. %, its promotion to the catalytic activity and water tolerance are plateaued.

Based on the above findings, a series of low grade non-refined feedstock of increasing acidities, waste cooking oil, crude rice bran oil, crude *Camelina* oil and crude *Jatropha* oil (fatty acid composition, acidity, acid value and water content thereof are listed in Table 6), were applied to the catalytic system using 95 wt. % ethanol. Their corresponding feedstock conversions were 98.5%, 99.1%, 99.4% and 99.8% respectively in 10 hrs, proving the wide-range application of MnGly towards biodiesel production.

conversion of 99.7% was achieved after 6 hrs of reaction under the optimal reaction conditions.

The effect of the reaction temperature on MnGly catalyzed biodiesel production was investigated in the range of 120° C. to 150° C. as depicted in part (b) of FIG. 4. The reaction temperature was found to be the most significant factor in the biodiesel production process as the feedstock conversion increased significantly from 25.9 to 81.6% in the studied range. This observation could be attributed to the inhibition of mass transfer resistance in the reaction medium in case of heterogeneous catalysis. Since the addition of solid MnGly catalyst into the reaction medium generates a three phase system of feedstock-ethanol-catalyst, the reaction could only occur at the interface of the triple phase. Thus, the rate of reaction is mass transfer-controlled. The enhancement in reaction temperature would accelerate the reaction rate by reducing the viscosity of feedstock through the improvement in the mass transfer resistance. Moreover, the increase in temperature increases the number of particles having sufficient energy to overcome the activation barrier so as to increase the rate of diffusion and the chance for collision between reactants and catalysts. Hence, the optimal reaction temperature is chosen to be 150° C.

In order to study the effect of feedstock-to-ethanol molar ratio on MnGly catalyzed biodiesel production, the reaction was investigated at 150° C. at four different ratios, 1:10, 1:20, 1:30 and 1:40. It was found that the feedstock conversion increased from 70.2 to 81.6% when the feedstock-to-ethanol molar ratio was varied from 1:10 to 1:20, but decreased steadily to 77.0% at the ratio of 1:40 as shown in

TABLE 6

Fatty acid composition, acidity, acid value and water content of the feedstock

| Feedstock | Fatty acid composition[a] (%) | | | | | | | Acidity (wt. %) | Acid value (mg$_{KOH}$/g) | Water content (wt. %) |
| --- | --- | --- | --- | --- | --- | --- | --- | --- | --- | --- |
| | $C_{16:0}$ | $C_{18:0}$ | $C_{18:1}$ | $C_{18:2}$ | $C_{18:3}$ | $C_{20:1}$ | $C_{22:1}$ | | | |
| Refined food grade canola oil | 5.00 | 2.68 | 63.06 | 22.82 | 6.44 | — | — | 0.11 | 0.22 | 0.13 |
| Waste cooking oil | 21.88 | 5.15 | 56.73 | 14.48 | 0.86 | 0.90 | — | 0.65 | 1.29 | 0.12 |
| Crude rice bran oil | 19.33 | 2.79 | 43.66 | 34.22 | — | — | — | 2.00 | 3.98 | 0.11 |
| Crude Camelina oil | 6.06 | 2.86 | 21.24 | 20.22 | 29.61 | 15.14 | 4.87 | 3.86 | 7.65 | 0.04 |
| Crude Jatropha oil | 14.55 | 6.95 | 40.82 | 37.68 | — | — | — | 4.93 | 9.78 | 0.13 |

NOTE:
[a]$C_{16:0}$ = palmitic acid,
$C_{18:0}$ = stearic acid,
$C_{18:1}$ = oleic acid,
$C_{18:2}$ = linoleic acid,
$C_{18:3}$ = linolenic acid,
$C_{20:1}$ = gadoleic acid and
$C_{22:1}$ = erucic acid.

Example 7 Effect of Reaction Parameters on Catalytic Activity of MnGly

The optimization of reaction conditions in the production of biodiesel is an important stage for industrial application in order to maximize the product yield and minimize the production cost. The relationship between the catalytic activity of MnGly and the reaction parameters, including reaction temperature, feedstock-to-ethanol molar ratio, and catalyst loading were evaluated. After the optimization process, the MnGly catalyzed biodiesel production with 95 wt. % ethanol was optimized at 150° C. with 1:20 feedstock-to-ethanol molar ratio under the assistance of 6 wt. % catalyst in the presence of 3 wt. % oleic acid. A feedstock part (c) of FIG. 4. As the transesterification reaction involves three consecutive reversible steps in converting a single triglyceride and three moles of ethanol into three FAEE, an excess feedstock-to-ethanol molar ratio is desirable to shift the equilibrium to the product side. However, further increase in the feedstock-to-ethanol molar ratio beyond the optimal molar ratio (1:20) lowers the concentration of feedstock in the reaction mixture which reduces the rate of reaction. In addition, the total amount of water present in 95 wt. % ethanol is higher when the feedstock-to-ethanol molar ratio increases, the chance of blockage of the active sites on the catalyst is enhanced and the catalytic activity of MnGly would be hindered. Thus, the optimal feedstock-to-ethanol molar ratio is found to be 1:20.

The effect of catalyst loading on the catalytic activity of MnGly was studied in the range of 2 to 10 wt. % at 150° C. with a feedstock-to-ethanol molar ratio of 1:20. As displayed from part (d) of FIG. 4, it demonstrates that the catalytic conversion increased significantly from 25.0% to the maximum point at 81.6% with an increase of catalyst loading from 2 to 6 wt. %. This initial improvement could be ascribed to the enhanced availability of active sites on the catalyst. Furthermore, because the presence of water in the reaction medium would compete with reactants for the active sites of catalyst, the availability of more active sites would lessen the negative impact of the competing reactions. However, further increase in the catalyst loading to 10 wt. % did not show any significant enhancement on feedstock conversion as the catalytic system might be saturated with the maximum number of active sites. Therefore, the catalyst loading is optimized at 6 wt. %.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method, comprising:
using manganese (II) glycerolate, cobalt (II) glycerolate, iron (II) glycerolate, or any combination thereof as a catalyst for catalyzing transesterification of esters or esterification of fatty acids;
wherein the manganese (II) glycerolate has average dimensions of 3.16 μm×2.38 μm, the cobalt (II) glycerolate has average dimensions of 6.98 μm×5.26 μm, and the iron (II) glycerolate has average dimensions of 0.55 μm×0.15 μm.

2. The method of claim 1, wherein the manganese (II) glycerolate has a surface basic strength of 6.8<H<7.2, the cobalt (II) glycerolate has a surface basic strength of 6.8<H<7.2, and the iron (II) glycerolate has a surface basic strength of 4.8<H<6.8.

3. A method for preparing a catalyst, the method comprising:
a) dissolving one or more metal acetate precursors into glycerol to yield a reaction mixture, wherein each of the one or more metal acetate precursors comprises cations being selected from the group consisting of manganese (II), cobalt (II), iron (II), and any combination thereof;
b) placing the reaction mixture in a pressurized microwave synthesis system for reaction; and
c) centrifuging a resulting precipitate, washing a centrifuged product with ethanol, and drying a resulting product to yield the catalyst, wherein the catalyst comprises a crystalline metal glycerolate selected from the group consisting of manganese (II) glycerolate, cobalt (II) glycerolate, iron (II) glycerolate, and any combination thereof;
wherein the manganese (II) glycerolate has average dimensions of 3.16 μm×x 2.38 μm, the cobalt (II) glycerolate has average dimensions of 6.98 μm×5.26 μm, and the iron (II) glycerolate has average dimensions of 0.55 μm×0.15 μm.

4. The method of claim 3, wherein a molar number of glycerol is at least 20 times of a molar number of the one or more metal acetate precursors.

5. The method of claim 3, wherein reaction parameters of the reaction in step b) are as follows: a reaction temperature is at least 80° C., a reaction time is at least 15 min, a reaction pressure is between 1 and 30 psi, and a microwave power is at least 100 Watts.

6. A method for a transesterification reaction, comprising:
a) providing a catalyst;
b) adding the catalyst, one or more alcohols, and a composition comprising one or more esters to a reactor to form a reaction mixture; and
c) stirring while heating the reaction mixture for reaction to form transesterification products;
wherein the catalyst comprises a crystalline metal glycerolate selected from the group consisting of manganese (II) glycerolate, cobalt (II) glycerolate, iron (II) glycerolate, and any combination thereof, wherein the manganese (II) glycerolate has average dimensions of 3.16 μm×2.38 μm, the cobalt (II) glycerolate has average dimensions of 6.98 μm×5.26 μm, and the iron (II) glycerolate has average dimensions of 0.55 μm×0.15 μm.

7. The method of claim 6, wherein the one or more alcohols are selected from the group consisting of methanol, ethanol, propanol, butanol, pentanol, hexanol, heptanol, octanol, and any isomers thereof.

8. The method of claim 6, wherein the one or more esters are triglycerides, wherein fatty acid portions of the triglycerides are selected from the group consisting of: acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-γ-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, neuronic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid, and octatriacontanoic acid.

9. The method of claim 6, wherein the one or more esters are a biodiesel feedstock.

10. The method of claim 9, wherein the one or more esters comprise plant-based oil, gutter oil, and/or grease trap waste.

11. The method of claim 6, wherein the composition comprising one or more esters further comprises one or more free fatty acids selected from the group consisting of acetic acid, propanoic acid, butanoic acid, pentanoic acid, hexanoic acid, heptanoic acid, octanoic acid, nonanoic acid, capric acid, undecanoic acid, lauric acid, tridecanoic acid, myristic acid, myristoleic acid, pentadecanoic acid, palmitic acid, palmitoleic acid, sapienic acid, heptadecanoic acid, stearic acid, oleic acid, elaidic acid, vaccenic acid, petroselinic acid, linoleic acid, linolelaidic acid, linolenic acid, stearidonic acid, nonadecanoic acid, eicosanoic acid, gadoleic acid, gondoic acid, paullinic acid, dihomo-γ-linolenic acid, mead acid, arachidonic acid, eicosapentaenoic acid, heneicosanoic acid, behenic acid, erucic acid, adrenic acid, docosahexaenoic acid, tricosanoic acid, lignoceric acid, nervonic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, ceroplastic acid, hexatriacontanoic acid, heptatriacontanoic acid, and octatriacontanoic acid for enhancing a reaction rate and conversion of the one or more esters.

12. The method of claim 6, wherein the reaction mixture is heated to a temperature of between 100° C. and 300° C.

13. The method of claim 6, wherein the number of moles of the one or more alcohols is at least 6 times of the number of moles of the composition comprising one or more esters.

14. The method of claim 6, wherein an addition of the catalyst is between 2 and 10 wt. %, based on a weight of the composition comprising one or more esters.

15. The method of claim 11, wherein the one or more free fatty acids account for between 0.1 and 100 wt. % of the composition comprising one or more esters.

16. The method of claim 7, wherein a water content in each of the one or more alcohols is between 0 and 80 wt. %, based on a weight of each of the one or more alcohols.

17. The method of claim 13, wherein the catalyst is manganese (II) glycerolate and the number of moles of the one or more alcohols is 20 times of the number of moles of the composition comprising one or more esters.

18. The method of claim 14, wherein the catalyst is manganese (II) glycerolate and an addition of the catalyst is 6 wt. %, based on a weight of the composition comprising one or more esters.

19. The method of claim 15, wherein the catalyst is manganese (II) glycerolate and the one or more free fatty acids account for between 3 and 100 wt. % of the composition comprising one or more esters.

20. The method of claim 7, wherein the catalyst is manganese (II) glycerolate, a reaction temperature is 150° C., the number of moles of the one or more alcohols is 20 times of the number of moles of the composition comprising one or more esters, and an addition of the catalyst is 6 wt. %, based on a weight of the composition comprising one or more esters.

* * * * *